United States Patent [19]

Wilk

[11] Patent Number: 5,458,131

[45] Date of Patent: * Oct. 17, 1995

[54] METHOD FOR USE IN INTRA-ABDOMINAL SURGERY

[76] Inventor: Peter J. Wilk, 185 W. End Ave., New York, N.Y. 10023

[*] Notice: The portion of the term of this patent subsequent to Mar. 29, 2011 has been disclaimed.

[21] Appl. No.: 181,700

[22] Filed: Jan. 14, 1994

Related U.S. Application Data

[63] Continuation-in-part of Ser. No. 934,914, Aug. 25, 1992, Pat. No. 5,297,536.

[51] Int. Cl.⁶ .................................................. A61B 1/00
[52] U.S. Cl. .................. 60/105; 606/140; 600/114; 600/159; 128/898
[58] Field of Search .................. 128/4, 8, 898, 128/6; 606/213, 139, 140, 144, 151, 46, 1; 604/54

[56] References Cited

U.S. PATENT DOCUMENTS

| | | |
|---|---|---|
| 3,643,653 | 2/1972 | Takahashi et al. |
| 3,760,810 | 9/1973 | Van Hoorn . |
| 4,103,680 | 8/1978 | Yoon . |
| 4,471,766 | 9/1984 | Terayama . |
| 4,735,194 | 4/1988 | Stiegmann . |
| 4,976,717 | 12/1990 | Boyle . |
| 5,224,497 | 7/1993 | Ehlers . |

*Primary Examiner*—Richard J. Apley
*Assistant Examiner*—Beverly A. Meindl
*Attorney, Agent, or Firm*—R. Neil Sudol; Henry D. Coleman

[57] ABSTRACT

A method for use in intra-abdominal surgery comprises, in accordance with the present invention, the steps of (a) inserting an incising instrument with an elongate shaft through a natural body opening into a natural body cavity of a patient, (b) manipulating the incising instrument from outside the patient to form a perforation in an internal wall of the natural internal body cavity, and (c) inserting a distal end of an elongate surgical instrument through the natural body opening, the natural body cavity and the perforation into an abdominal cavity of the patient upon formation of the perforation. Further steps of the method include (d) inserting a distal end of an endoscope into the abdominal cavity, (e) operating the surgical instrument to perform a surgical operation on an organ in the abdominal cavity, (f) viewing the surgical operation via the endoscope, (g) withdrawing the surgical instrument and the endoscope from the abdominal cavity upon completion of the surgical operation, and (h) closing the perforation.

31 Claims, 4 Drawing Sheets

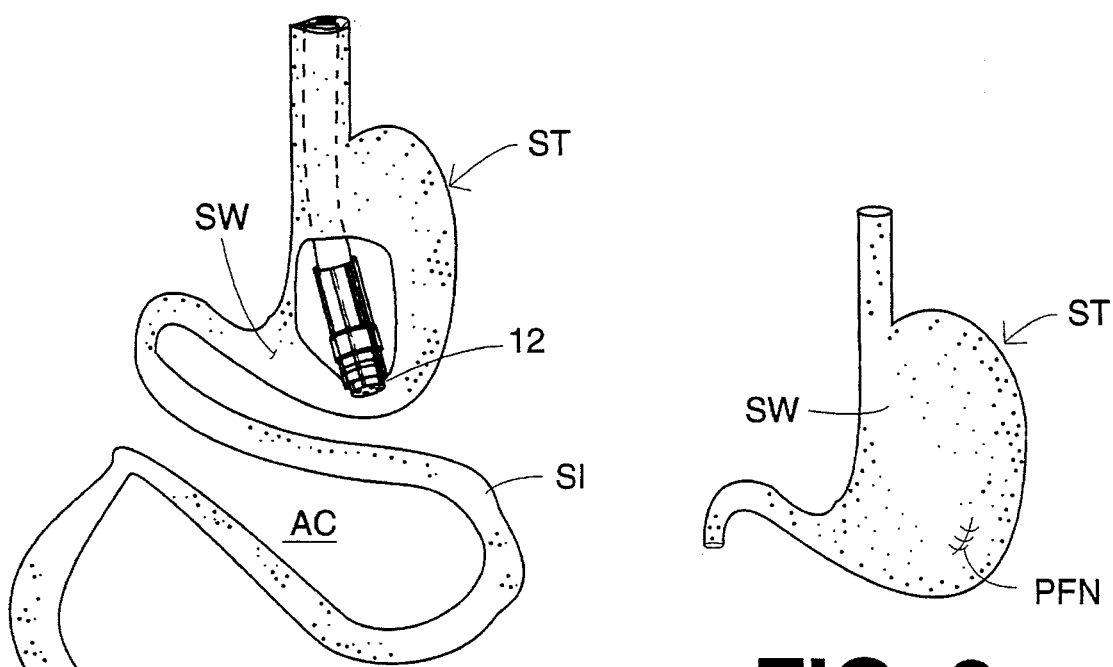
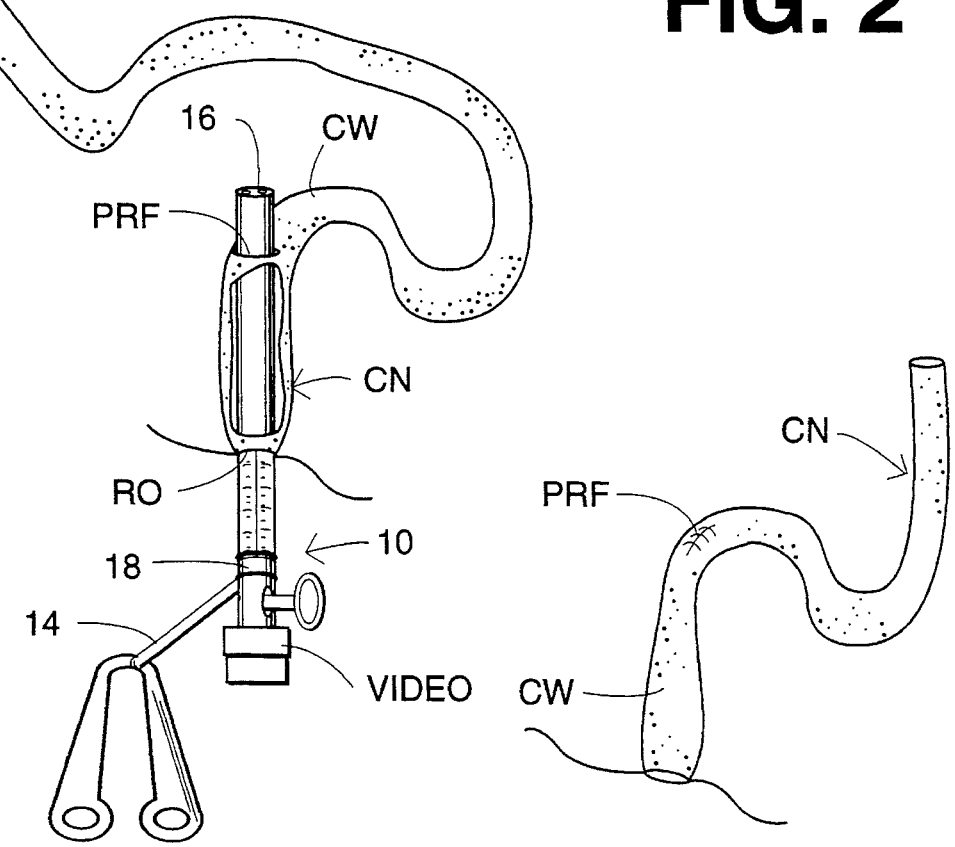
FIG. 1
FIG. 2
FIG. 3

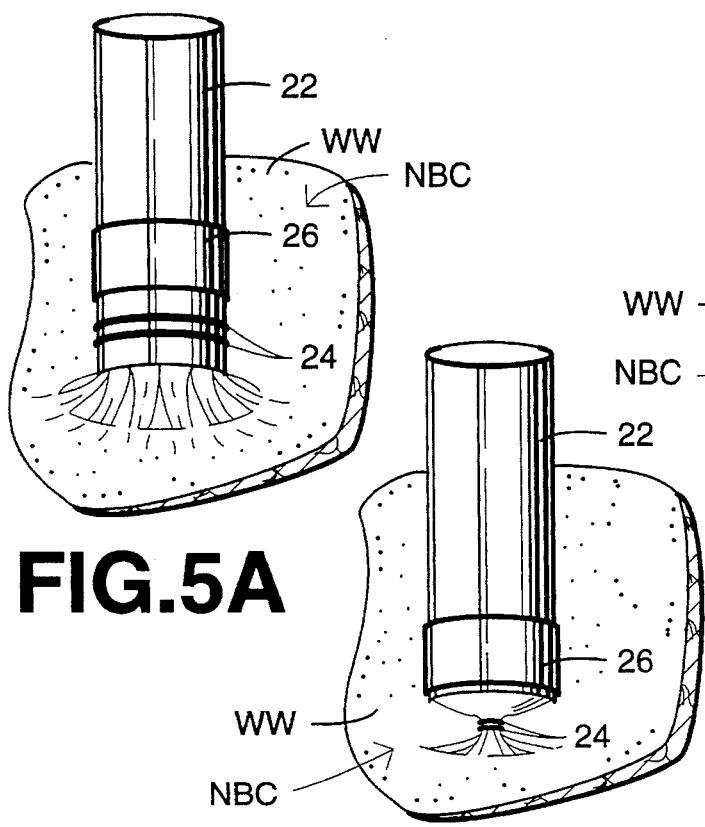
FIG.5A
FIG. 5B
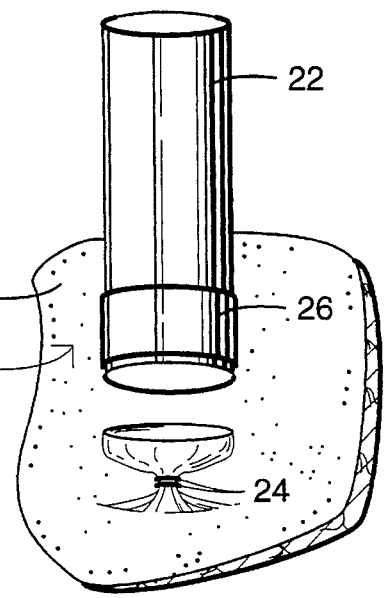
FIG. 5C
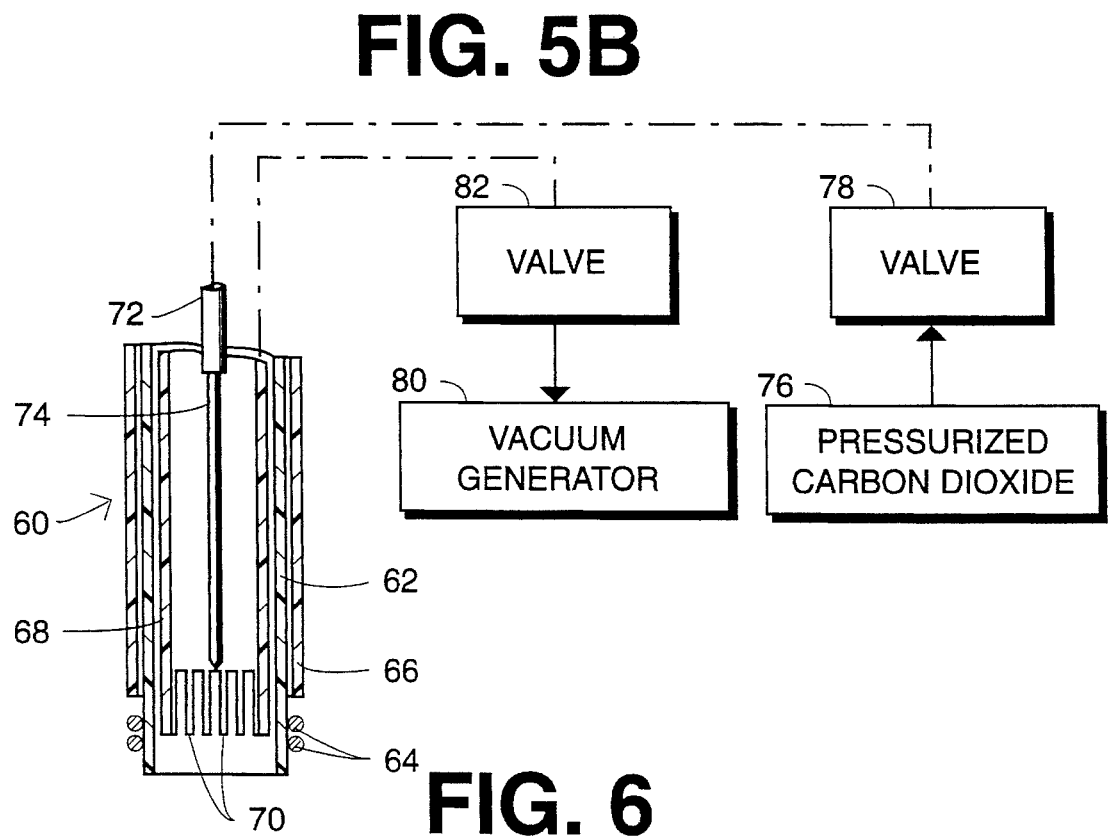
FIG. 6

METHOD FOR USE IN INTRA-ABDOMINAL SURGERY

CROSS-REFERENCE TO A RELATED APPLICATION

This application is a continuation-in-part of commonly owned application Ser. No. 07/934,914 filed Aug. 25, 1992, now U.S. Pat. No. 5,297,536.

BACKGROUND OF THE INVENTION

This invention relates to a method for use in intraabdominal surgery.

Intra-abdominal surgery has been conventionally performed by forming an incision in the abdominal wall and operating on internal body organs through the incision. This method of surgery invariably results in substantial blood loss, as well as extended pain to the patient after surgery has been completed.

The disadvantages of conventional intra-abdominal surgery has been subtantially reduced by the technique of laparoscopic surgery wherein access to abdominal organs is obtained through trocar sleeves or laparoscopic cannulas disposed in respective perforations formed in the abdominal wall of the patient by trocars. Hospital stays and patient trauma are reduced.

OBJECT OF THE INVENTION

An object of the present invention is to provide a new method for the performance of intra-abdominal surgery.

Another object of the present invention is to provide such a method which reduces the incisions in the abdominal wall required during intra-abdominal surgery.

Another, more particular, object of the present invention is to provide an endoscopic method for obtaining access to abdominal organs.

These and other objects of the invention will be apparent from the descriptions and illustrations provided herein.

SUMMARY OF THE INVENTION

A method for use in intra-abdominal surgery comprises, in accordance with the present invention, the steps of (a) inserting an incising instrument with an elongate shaft through a natural body opening into a natural body cavity of a patient, (b) manipulating the incising instrument from outside the patient to form a perforation in an internal wall of the natural internal body cavity, and (c) inserting a distal end of an elongate surgical instrument through the natural body opening, the natural body cavity and the perforation into an abdominal cavity of the patient upon formation of the perforation. Further steps of the method include (d) inserting a distal end of an endoscope into the abdominal cavity, (e) operating the surgical instrument to perform a surgical operation on an organ in the abdominal cavity, (f) viewing the surgical operation via the endoscope, (g) withdrawing the surgical instrument and the endoscope from the abdominal cavity upon completion of the surgical operation, and (h) closing the perforation.

According to another feature of the present invention, the distal end of the endoscope is inserted into the abdominal cavity through the perforation formed by the incising instrument. In that event, the method may further comprise the step of inserting an ancillary tube through the natural body opening and into the natural body cavity prior to the manipulation of the incising instrument to form the perforation. The endoscope is inserted through the ancillary tube. In addition, a fluid tight engagement is formed between a distal end of the ancillary tube and the internal wall of the natural body cavity prior to the manipulation of the incising instrument to form the perforation. The endoscope is inserted through the ancillary tube and the perforation.

According to another feature of the present invention, the abdominal cavity is insufflated prior to the insertion of the distal end of the endoscope into the abdominal cavity. The abdominal cavity may be insufflated through the ancillary tube and the perforation. Alternatively, insufflation may be implemented via a Veress needle inserted through the abdominal wall or through another perforation in the internal wall of the natural body cavity. That other perforation is formed by the Veress needle itself.

According to an additional feature of the present invention, the endoscope is inserted into the abdominal cavity through the perforation prior to insertion of the distal end of the surgical instrument. In that case, the distal end of the surgical instrument may be inserted into the abdominal cavity through a biopsy channel of the endoscope or through a channel in a sheath on the endoscope.

In an alternative procedure in accordance with the present invention, the distal end of the endoscope is inserted into the abdominal cavity via an additional perforation formed in an internal cavity of the patient. That internal cavity may be the same as the natural body cavity through which the surgical instrument is inserted into the abdominal cavity. Alternatively, the endoscope may be inserted through another internal organ. For example, the surgical instrument may be inserted through the stomach, while the endoscope is inserted through the colon or the vagina.

According to a further feature of the present invention, the method also includes the step of obtaining visual feedback as to position of a distal end of the incising instrument prior to the step of manipulating. That visual feedback may be obtained via the endoscope or, alternatively, via radiographic or X-ray equipment.

A method for use in intra-abdominal surgery comprises, in accordance with another conceptualization of the present invention, the steps of (i) inserting an endoscope through a natural body opening into a natural body cavity of a patient, (ii) inserting an endoscopic type incising instrument through the natural body opening into the natural body cavity, (iii) manipulating the incising instrument from outside the patient to form a perforation in an internal wall of the natural internal body cavity, (iv) moving a distal end of the endoscope through the perforation, (v) using the endoscope to visually inspect internal body tissues in an abdominal cavity of the patient, (vi) inserting a distal end of an elongate surgical instrument into the abdominal cavity of the patient, (vii) executing a surgical operation on the internal body tissues by manipulating the surgical instrument from outside the patient, (viii) upon completion of the surgical operation, withdrawing the surgical instrument and the endoscope from the abdominal cavity, (ix) closing the perforation, and (x) withdrawing the endoscope from the natural body cavity.

According to another feature of the present invention, the distal end of the surgical instrument is inserted through an additional perforation formed in a wall of an internal organ of the patient. The additional perforation is closed upon withdrawing of the surgical instrument from the abdominal cavity. The additional perforation may be formed in the same internal wall as the perforation through which the distal end of the endoscope is inserted into the abdominal cavity. Alternatively, the distal end of the surgical instrument may be passed through a biopsy channel of the endoscope.

A method in accordance with the present invention reduces trauma to the individual even more than laparoscopic procedures. Hospital convalescence stays are even shorter.

BRIEF DESCRIPTION OF THE DRAWING

FIG. 1 is a diagram of the gastro-intestinal tract, showing two points of entry from the tract into the abdominal cavity in a surgical procedure in accordance with the present invention.

FIG. 2 is a diagram of the stomach, showing closure of an entry point into the abdominal cavity upon completion of surgery in accordance with the present invention.

FIG. 3 is a diagram of the sigmoidal colon, showing closure of an entry point into the abdominal cavity upon completion of surgery in accordance with the present invention.

FIGS. 5A–5C are partially cross-sectional views of the stomach and partially side elevational views of the assembly of FIG. 4, showing successive steps in the use of the assembly in a method in accordance with the present invention.

FIG. 6 is partially a block diagram and partially a longitudinal cross-sectional view of a surgical assembly for use in a surgical method in accordance with the present invention.

DETAILED DESCRIPTION

Figure 4:
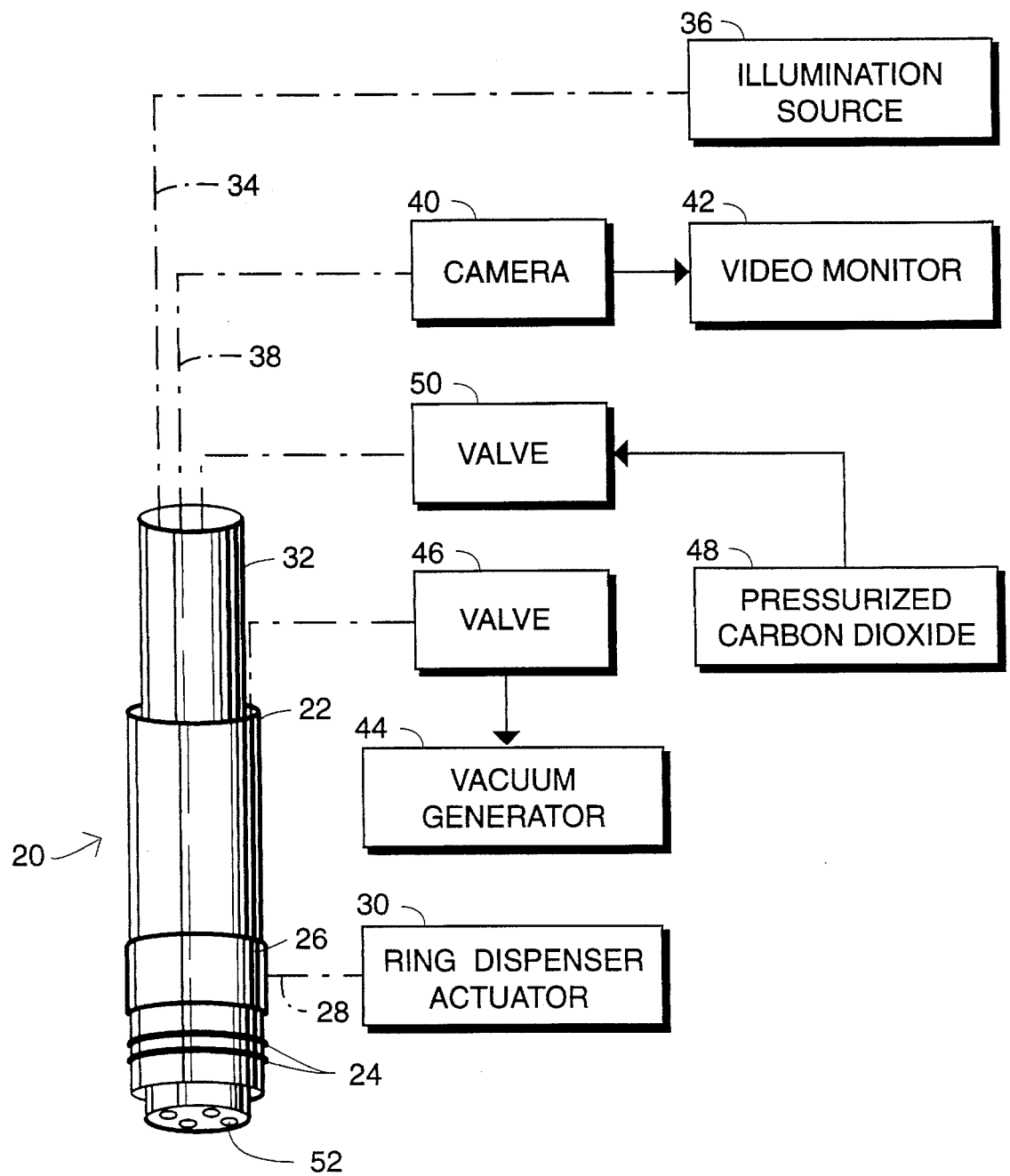
FIG. 4 is partially a block diagram and partially a schematic side perspective view of a surgical assembly for use in a surgical method in accordance with the present invention.

As illustrated in FIG. 1, intra-abdominal surgery is performed without the formation of an incision in the abdominal wall of the patient. Instead, endoscopic surgical instruments 10 or 12 are inserted into the patient through a natural body opening such as the anus or rectal orifice RO or the mouth (not illustrated) and through a wall CW or SW of a natural body cavity or organ such as the colon CN or the stomach ST. Intra-abdominal surgery can alternatively be performed on a female patient by inserting surgical instruments into the patient's abdominal cavity through the vagina and the wall of the cul-de-sac.

In performing surgery though the colon, for example, endoscope 10 is inserted through rectal orifice RO into the sigmoidal section of the colon CN and used to visually inspect the internal surfaces thereof for purposes of determining a suitable point of entry. An endoscopic type incising instrument 14 is inserted into the colon CN along a passage established by the endoscope, for example, through a biopsy channel 16 of the insertion member 18 of endoscope 10 or through an ancillary channel in an endoscopic sheath (not shown). Such a sheath with collapsed biopsy channels is disclosed in U.S. Pat. Nos. 4,646,722 and 5,025,778 to Silverstein et al. the disclosure of which is hereby incorporated by reference herein.

Incising instrument 14 is manipulated from outside the patient to form a perforation PRF in wall CW of the sigmoidal portion of colon CN. Subsequently, a distal end of endoscope insertion member 18 is inserted through perforation PRF, the endoscope being used then to visually inspect internal body tissues, e.g., small intestine SI, colon CN, etc., in the abdominal cavity AC of the patient. Upon locating a surgical site, a surgical operation is executed on the internal body tissues by manipulating an endoscopic surgical instrument (e.g., incising instrument 14) passed along endoscope insertion member 18 through rectal orifice RO, colon CN and perforation PRF.

A surgical operation performable in an abdominal cavity may include, for example, a colecystectomy, a ressection of the colon, repair of traumatized organs, etc. Many operations which can presently be executed via laparoscopic techniques may be performed endoscopically through a perforation formed in a natural body cavity or organ such as the stomach ST, the colon CN or the vagina.

Such endoscopic surgery will be facilitated by endoscopic instruments (graspers, forceps, scalpels, staplers, suturing devices, irrigators, cauterization devices, etc.) having flexible distal ends which are steerable via cables extending along the lengths of the instruments from respective control knobs at the proximal ends of the instruments. This steering enables greater control of the surgical instruments.

Upon completion of the intra-abdominal surgery, the endoscopic surgical instrument(s) (e.g., 14) and endoscope 10 are withdrawn from the abdominal cavity AC through perforation PRF. Perforation PRF is then closed and endoscope 10 is withdrawn from colon CN. FIG. 3 shows the colon CN with perforation PRF closed upon completion of the surgery. FIG. 2 shows closure of a perforation PFN formed in stomach ST during intra-abdominal surgery through the stomach ST as described above and hereinafter.

As illustrated in FIG. 4, an endoscopic assembly 20 for use in performing intra-abdominal surgery through a natural body cavity comprises an outer tube 22 provided at a distal end with a pair of O rings 24 and a sleeve 26 for sliding O rings 24 off the distal end of tube 22 at the termination of an intra-abdominal surgical procedure. Sleeve 26 is connected via a link 28 such as a rod or pair of rods to an actuator 30 disposed at the proximal end of the instrument assembly 20.

Endoscopic instrument assembly 20 further comprises an endoscopic insertion member 32 having a fiber optic illumination guide 34 connected to a light source 36 and a fiber optic image guide 38 connected to a video camera 40 (e.g., a charge coupled device). Camera 40 is in turn coupled to a video monitor 42 for enabling visual inspection of an image carried by guide 38. A vacuum generator 44 is connected to tube 22 via a valve 46, while a pressurized source 48 of a gas such as carbon dioxide communicates via a valve 50 with a biopsy channel 52 of endoscopic insertion member 32.

As illustrated in FIG. 5A, prior to the incising of a wall WW of a natural body cavity or organ NBC, a distal end of tube 22 is brought into engagement with the wall. Suction is applied to the wall WW by opening valve 46 to connect vacuum generator 44 to tube 22.

Tube 22 and endoscopic insertion member 32 may be inserted together through a natural body opening into an organ, endoscopic insertion member 32 being manipulated to facilitate visual inspection of the internal tissues of the patient via monitor 42. Upon selection of a suitable entry site, endoscopic insertion member 32 is withdrawn at least partially from tube 22 to facilitate the formation of a negative-pressure connection between the distal end of tube 22 and the wall of the organ.

Pressurized carbon dioxide source 48 may be connected to a tubular instrument (not shown) slidably inserted into biopsy channel 52 of endoscopic insertion member 32, the tubular instrument being formed at a distal end with a needle (not shown) for piercing the wall WW of the organ. Upon a piercing of the wall and an entry of the needle into the abdominal cavity, valve 50 is actuated to connect source 48 to the tubular member for a time long enough to insufflate the abdominal cavity.

After a suitable expansion of the abdomen has been attained, the insufflation needle and tubular member are withdrawn from biopsy channel 52 and replaced with an endoscopic incising instrument as described hereinabove with reference to instrument 14 of FIG. 1. The incising instrument is manipulated from outside the patient to form a perforation in the wall WW of the natural cavity or organ.

Upon the completion of an intra-abdominal operation, executed via instruments inserted through biopsy channel 52 and other biopsy channels of endoscopic insertion member 32, and upon the withdrawal of such instruments and endoscopic insertion member 32 from the abdominal cavity, actuator 30 is operated to slide sleeve 26 in a distal direction over the endoscopic insertion member, thereby sliding O rings 24 onto wall WW, as illustrated in FIG. 5B. Rings 24 serve to clamp the tissues of wall WW, thereby closing the perforation through which an operation has been performed. As shown in FIG. 5C, upon the disposition of rings 24, vacuum generator 44 is disconnected from tube 22 and the distal end of the tube is disengaged from wall WW. Endoscopic insertion member 32 may be used at that juncture to inspect the closure. Subsequently, insertion member 32 and tube 22 are removed from the patient.

As illustrated in FIG. 6, another instrument assembly 60 for use in performing intra-abdominal surgery via a natural body opening and an associated internal organ of the patient comprises a first tubular member 62 provided at a distal end with a pair of elastic O rings 64. A dispensing tube 66 slidably coaxial with and surrounding tube 62 is provided for pushing rings 64 off of tubular member 62 at the termination of an operation. An auxiliary tubular member 68 inserted inside tubular member 62 is formed at a distal end with a plurality of longitudinally extending prongs or barbs 70.

FIG. 6 additionally shows a hollow rod 72 provided at a distal end with a hollow needle 74. Rod 72 communicates with a source 76 of pressurized carbon dioxide via a valve 78. A vacuum generator or suction source 80 is connected to tubular member 62 via a valve 82.

Instrument assembly 60 may be used in a manner similar to the procedure described hereinabove with reference to FIGS. 4 and 5A–5C. Upon the locating of a suitable abdominal entry site in a wall of an internal organ, with or without the use of an endoscope, tubular member 62 is pushed in a distal direction so that the distal end of the tubular member is brought into engagement with the wall of the organ. Valve 82 is then operated to connect suction source 80 to tubular member 62, thereby sucking the wall of the organ into the distal end of tubular member 62. Inner tubular member 68 is then pushed in a distal direction so that prongs 70 are at least partially embedded in the tissues of the organ wall.

If an endoscope has been inserted through inner tubular member 68 to aid in the location of an entry point, the endoscope may be removed prior to the insertion of rod 72 and needle 74. Alternatively, as discussed above, rod 72 and needle 74 may be inserted through a biopsy channel of the endoscope. Needle 74 is used to insufflate the abdominal cavity and is withdrawn. The remainder of the procedure is clear.

Figure 7:
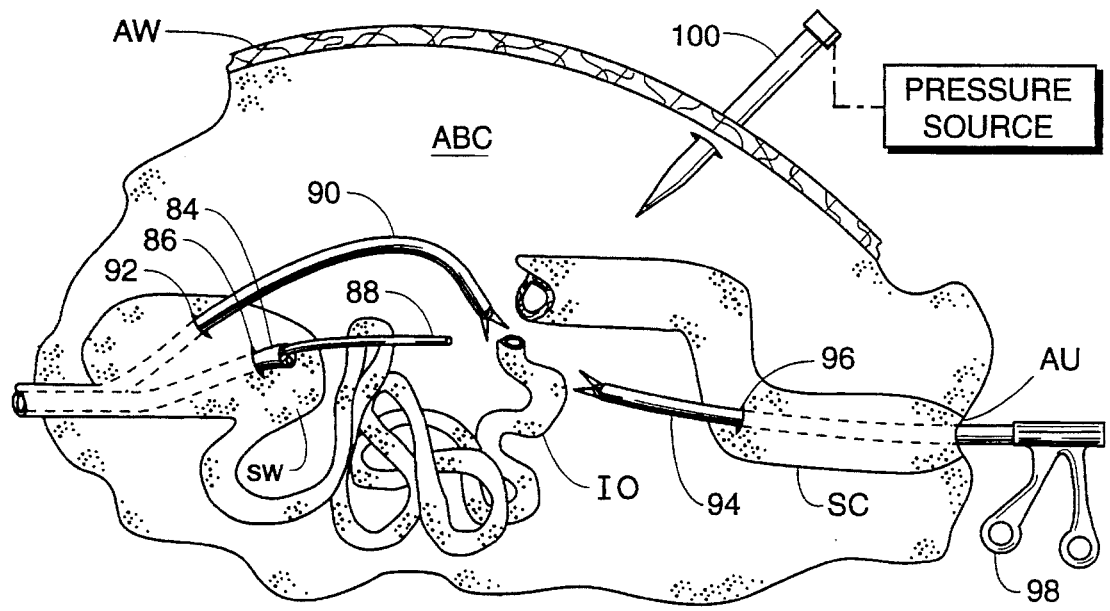
FIG. 7 is partially a block diagram and partially schematic perspective views of endoscopic operating instrumentation and partially a schematic cross-sectional view of a patient's abdomen, showing a stage in an endoscopic operating procedure in accordance with the present invention.

As illustrated in FIG. 7, a distal end of a flexible endoscope 84 is inserted through a perforation 86 formed in a wall of stomach SW as described hereinabove with reference to FIG. 1. Upon insertion of the distal end of the endoscope 84 into an abdominal cavity ABC of the patient through perforation 86, the endoscope is used to visually inspect an internal organ prior to and during a surgical operation on the organ. A distal end of a first endoscopic surgical instrument 88 such as a laser fiber is inserted into abdominal cavity ABC through a biopsy channel of endoscope 84. A distal end of another endoscopic type surgical instrument 90 is inserted into abdominal cavity ABC through another perforation 92 formed in stomach SW by an incising instrument (not shown) as described hereinabove with respect to FIG. 1. A distal end of a third elongate flexible surgical instrument 94 is inserted through a perforation 96 formed in a sigmoidal colon SC of the patient.

Endoscopic surgical instruments 88, 90 and 94 are preferably provided with mechanisms for controllably bending the distal ends of the instruments. Such distal end orientation control may be implemented through cables (not shown) extending longitudinally through the instruments to actuators 98 at the proximal ends of the respective instruments. Such cables systems are conventionally used in flexible endoscopes. Alternative systems for distal end orientation control of endoscopic instruments include, for example, hydraulic circuits.

As illustrated in FIG. 7, abdominal cavity ABC is pressurized or insufflated prior to the insertion of endoscope 84 by a conventional Veress needle 100 inserted through an abdominal wall AW of the patient. Needle 100 may be retained in place during the operation to ensure adequate pneumoperitoneum.

Alternatively, abdominal cavity ABC may be pressurized or insufflated prior to the insertion of endoscope 84 through perforation 86 by a stream of gas guided along the insertion path of endoscope 84, e.g., via a biopsy channel of the endoscope.

Pursuant to another alternative procedure, a Veress needle or similar instrument may be separately inserted through a natural body opening such as the anus AU. The needle pierces the colon wall and enters abdominal cavity ABC. Of course, such a procedure is done under visual inspection.

Figure 8:
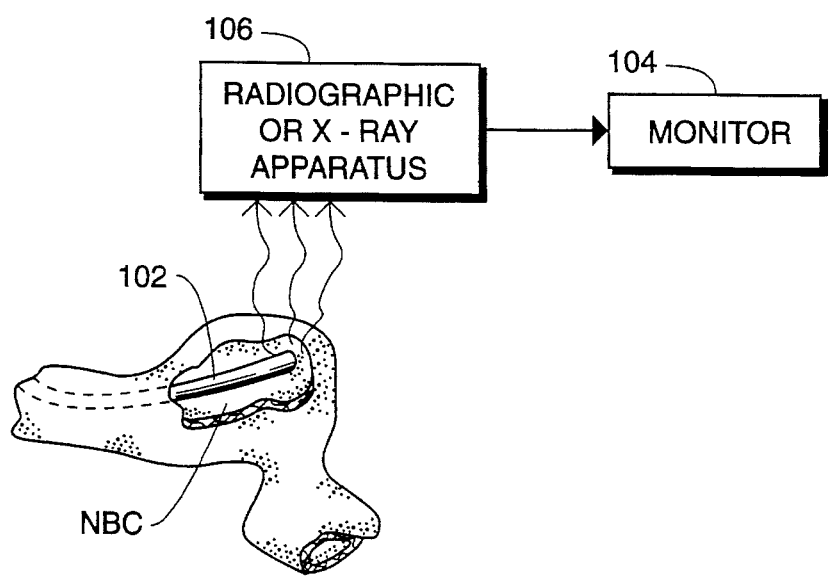
FIG. 8 is partially a block diagram and partially a schematic perspective view of an endoscopic incising instrument and partially a broken away view of a patient's colon, showing a stage in an endoscopic operating procedure in accordance with the present invention.

As illustrated in FIG. 8, a distal end of an incising instrument (or Veress needle) 102 may be guided to an insertion location by monitoring an image displayed on a monitor 104 in response to signals generated by a radiographic or X-ray apparatus 106. Incising instrument 102 and the procedure of FIG. 8 may be used to form perforations 86, 92, and 96 (FIG. 7). Alternatively, an endoscope such as endoscope 84 may be used to monitor the formation of those internal perforations.

Accordingly, incising instrument 102 is inserted through a natural body opening (such as the mouth, anus, or vagina) into a natural body cavity NBC of a patient. Incising instrument 102 is manipulated from outside the patient to form perforation 86, 92, or 96 in an internal wall of the natural internal body cavity. Subsequently, the distal end of an elongate, preferably flexible, surgical instrument, e.g., 90 or 94 in FIG. 7, is inserted through the natural body opening, the natural body cavity NBC and the perforation into abdominal cavity ABC of the patient.

As discussed above, the surgical instruments 88, 90 and 92 are operated or manipulated from outside the patient to perform surgical operations on organ IO in abdominal cavity ABC (FIG. 7). The surgical operation is visually monitored via endoscope 84. Subsequently, upon completion of the surgical operation(s), surgical instruments 88, 90 and 94, as well as endoscope 84, are withdrawn from abdominal cavity ABC. Perforations 86, 92, and 96 are then closed as described above.

As discussed above, further endoscopic surgical instruments may be inserted into abdominal cavity ABC along collapsible biopsy channels in a sheath (not shown) on endoscope 84.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method for use in intra-abdominal surgery, comprising the steps of:

inserting an incising instrument with an elongate shaft through a natural body opening into a natural body cavity of a patient;

manipulating said incising instrument from outside the patient to form a perforation in an internal wall of said natural internal body cavity;

upon formation of said perforation, inserting a distal end of an elongate surgical instrument through said natural body opening, said natural body cavity and said perforation into an abdominal cavity of the patient;

inserting a distal end of an endoscope into said abdominal cavity;

operating said surgical instrument to perform a surgical operation on an organ in said abdominal cavity;

during said step of operating, viewing the surgical operation via said endoscope;

upon completion of said surgical operation, withdrawing said surgical instrument and said endoscope from said abdominal cavity; and closing said perforation.

2. The method defined in claim 1 wherein said distal end of said endoscope is inserted into said abdominal cavity through said perforation.

3. The method defined in claim 2, further comprising the step of inserting an ancillary tube through said natural body opening and into said natural body cavity prior to said step of manipulating said incising instrument to form said perforation, said endoscope being inserted through said ancillary tube.

4. The device defined in claim 3, further comprising the step of forming a fluid tight engagement between a distal end of said ancillary tube and said internal wall of said natural body cavity prior to said step of manipulating said incising instrument to form said perforation, said endoscope being inserted through said ancillary tube and said perforation.

5. The method defined in claim 4, further comprising the steps of insufflating said abdominal cavity through said ancillary tube and said perforation prior to said step of inserting said distal end of said endoscope into said abdominal cavity.

6. The method defined in claim 2 wherein said endoscope is inserted into said abdominal cavity through said perforation prior to insertion of said distal end of said surgical instrument.

7. The method defined in claim 2 wherein said distal end of said surgical instrument is inserted into said abdominal cavity through a biopsy channel of said endoscope.

8. The method defined in claim 2 wherein said endoscope is provided with a sheath having an expandable channel, said incising instrument being inserted through said channel upon insertion of said endoscope through said natural body opening and into said natural body cavity.

9. The method defined in claim 1 wherein said distal end of said endoscope is inserted into said abdominal cavity via an additional perforation formed in an internal cavity of the patient.

10. The method defined in claim 9 wherein said internal cavity is said natural body cavity.

11. The method defined in claim 9 wherein said internal cavity is a cavity different from said natural body cavity.

12. The method defined in claim 1, further comprising the steps of insufflating said abdominal cavity prior to said step of inserting said distal end of said endoscope into said abdominal cavity.

13. The method defined in claim 12 wherein said step of insufflating includes the step of inserting a Veress needle through an abdominal wall of the patient into said abdominal cavity.

14. The method defined in claim 12 wherein said step of insufflating said abdominal cavity includes the step of guiding a pressurizing gas through said perforation into said abdominal cavity.

15. The method defined in claim 1, further comprising the step of obtaining visual feedback as to position of a distal end of said incising instrument prior to said step of manipulating.

16. The method defined in claim 15 wherein said step of obtaining includes the step of operating radiographic equipment.

17. The method defined in claim 15 wherein said step of obtaining includes the step of operating an X-ray apparatus.

18. The method defined in claim 15 wherein said step of obtaining includes the steps of inserting an endoscope through said natural body opening into said natural body cavity.

19. The method defined in claim 1 wherein said surgical instrument is different from said incising instrument, further comprising the step of moving said incising instrument from said perforation upon formation thereof to enable insertion of said distal end of said surgical instrument through said perforation.

20. The method defined in claim 1 wherein said natural body opening is the mouth and said natural body cavity is the stomach.

21. The method defined in claim 1 wherein said natural body opening is the anus and said natural body cavity is the colon.

22. The method defined in claim 1 wherein said natural body opening is the vaginal orifice and said natural body cavity is the vaginal canal.

23. A method for use in intra-abdominal surgery, comprising the steps of:

inserting an endoscope through a natural body opening into a natural body cavity of a patient;

inserting an endoscopic type incising instrument through said natural body opening into said natural body cavity;

manipulating said incising instrument from outside the patient to form a perforation in an internal wall of said natural internal body cavity;

moving a distal end of said endoscope through said perforation;

using said endoscope to visually inspect internal body tissues in an abdominal cavity of the patient;

inserting a distal end of an elongate surgical instrument into said abdominal cavity of the patient;

executing a surgical operation on said internal body tissues by manipulating said surgical instrument from outside the patient;

upon completion of said surgical operation, withdrawing said surgical instrument and said endoscope from said abdominal cavity;

closing said perforation; and withdrawing said endoscope from said natural body cavity.

24. The method defined in claim 23 wherein said step of inserting said distal end of said surgical instrument includes the steps of forming an additional perforation in a wall of an internal organ of the patient and inserting said distal end of said surgical instrument through said additional perforation, further comprising the step of closing said additional perforation upon withdrawing of said surgical instrument from said abdominal cavity.

25. The method defined in claim 24 wherein said wall of said internal organ is the same as said internal wall.

26. The method defined in claim 23 wherein said step of inserting said distal end of said surgical instrument includes the step of passing said surgical instrument through a biopsy channel of said endoscope.

27. The method defined in claim 23, further comprising the step of inserting an ancillary tube through said natural body opening and into said natural body cavity prior to said step of manipulating said incising instrument to form said perforation, said endoscope being inserted through said ancillary tube.

28. The device defined in claim 27, further comprising the step of forming a fluid tight engagement between a distal end of said ancillary tube and said internal wall of said natural body cavity prior to said step of manipulating said incising instrument to form said perforation, said endoscope being inserted through said ancillary tube and said perforation.

29. The method defined in claim 23, further comprising the steps of insufflating said abdominal cavity prior to said step of inserting said distal end of said endoscope into said abdominal cavity.

30. The method defined in claim 29 wherein said step of insufflating includes the step of inserting a Veress needle through an abdominal wall of the patient into said abdominal cavity.

31. The method defined in claim 29 wherein said step of insufflating said abdominal cavity includes the step of guiding a pressurizing gas through said perforation into said abdominal cavity.

* * * * *